United States Patent [19]

Shimamune et al.

[11] Patent Number: 5,034,186

[45] Date of Patent: Jul. 23, 1991

[54] PROCESS FOR PROVIDING TITANIUM COMPOSITE HAVING A POROUS SURFACE

[75] Inventors: Takayuki Shimamune, Tokyo; Hideo Sato, Chiba; Masashi Hosonuma, Kanagawa, all of Japan

[73] Assignee: Permelec Electrode Ltd., Kanagawa, Japan

[21] Appl. No.: 932,551

[22] Filed: Nov. 20, 1986

[30] Foreign Application Priority Data

Nov. 20, 1985 [JP] Japan ................. 60-258728

[51] Int. Cl.$^5$ ................. B22F 7/00
[52] U.S. Cl. ................. 419/9; 419/23; 419/20; 419/36; 419/37; 419/57; 419/53; 428/550; 428/553; 427/191; 427/226; 427/247; 427/336; 427/352; 623/16
[58] Field of Search ............... 427/191, 226, 247, 336, 427/352; 428/550, 553; 419/23, 36, 9, 37, 53, 26, 57; 623/16

[56] References Cited

U.S. PATENT DOCUMENTS

| | | | |
|---|---|---|---|
| 2,447,980 | 8/1948 | Hensel | 427/247 |
| 3,437,457 | 4/1969 | Fisher | 29/182.2 |
| 3,762,026 | 10/1973 | Shapiro | 29/420 |
| 4,644,942 | 2/1987 | Sump | 427/191 |

FOREIGN PATENT DOCUMENTS

| | | |
|---|---|---|
| WO8303105 | 9/1983 | Fed. Rep. of Germany . |
| 588062 | 9/1944 | United Kingdom . |
| 586062 | 3/1947 | United Kingdom . |
| 701690 | 12/1953 | United Kingdom . |
| 995901 | 6/1965 | United Kingdom . |
| 1068121 | 5/1967 | United Kingdom . |
| 1465501 | 2/1977 | United Kingdom . |
| 1550010 | 8/1979 | United Kingdom . |
| 2142544 | 1/1985 | United Kingdom . |

OTHER PUBLICATIONS

Uhlig, *Corrosion and Corrosion Control*, 2nd ed., 1971, p. 29.

*Primary Examiner*—Stephen J. Lechert, Jr.
*Attorney, Agent, or Firm*—Sughrue, Mion, Zinn, Macpeak & Seas

[57] ABSTRACT

A titanium or titanium alloy composite having a porous surface layer, which comprises a titanium or titanium alloy substrate and a porous titanium or titanium alloy layer that adheres strongly to said substrate, said porous layer being formed by first providing said substrate with a firmly adhering sinter of a mixture of a titanium or titanium alloy powder and a magnesium powder, and then removing magnesium from the sinter. A process for producing a titanium or titanium alloy composite having a porous surface layer, comprising: providing a coating composition comprising a binder added to a mixture of a titanium or titanium alloy powder and a magnesium powder; applying said composition to the surface of a titanium or titanium alloy substrate; heating the substrate at a temperature of from 650° to 800° C. in vacuo or an inert atmosphere so as to form a sinter of the powders of titanium or titanium alloy and magnesium which firmly adheres to said substrate; and removing magnesium from said sinter.

3 Claims, 1 Drawing Sheet

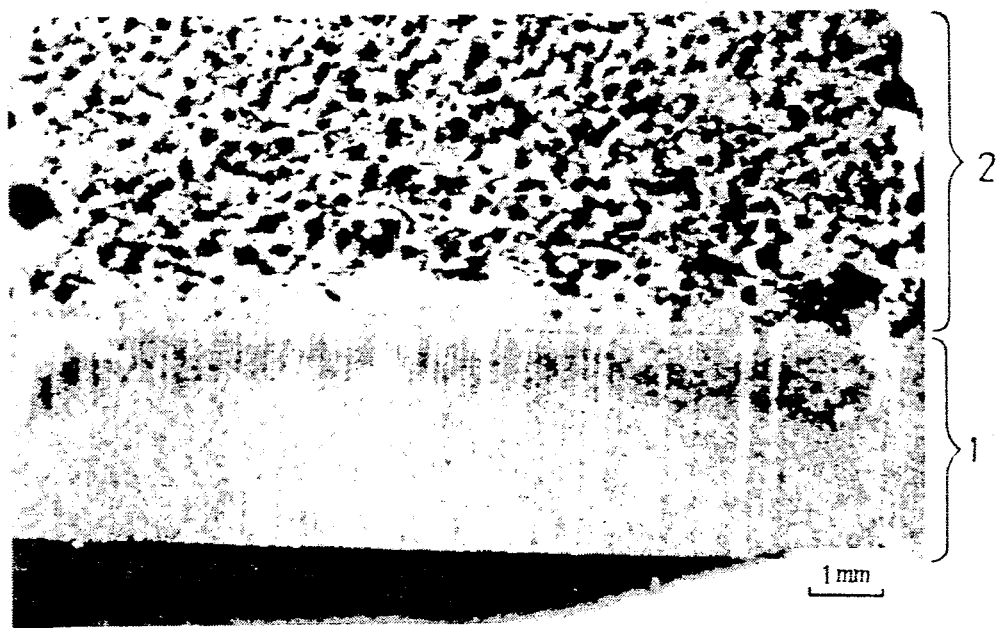

5,034,186

PROCESS FOR PROVIDING TITANIUM COMPOSITE HAVING A POROUS SURFACE

FIELD OF THE INVENTION

The present invention relates to a titanium or titanium alloy composite having a porous surface. More particularly, the present invention relates to a titanium or titanium alloy composite suitable for use as an electrolytic electrode substrate, a catalyst support or a metallic material for biocompatible implants, as well as to a process for producing such a composite.

BACKGROUND OF THE INVENTION

Being known as a metallic material having superior mechanical strength and chemical durability, titanium has long been used in various fields. For instance, titanium-based electrodes are exclusively used in modern electrolytic equipment for producing chlorine and sodium hydroxide by electrolysis of aqueous sodium chloride. The titanium-based electrodes comprise a titanium substrate coated with an electrode active material and, in order to ensure higher electrode performance as manifested by prolonged service life and lower overpotential, the substrate desirably has an adequately large surface area and strong adhesion to the coating. To this end, it has been proposed to roughen the surface of the titanium substrate by either blasting or etching, but the increase in surface area can be achieved only with respect to a shallow surface layer and the anchor effect attained is not strong enough to provide firm adhesion to the coating material.

Porous titanium materials which are generally spongy or fibrous are known (see, for example, Japanese Patent Application (OPI) No. 8416/80 (the term "OPI" means an unexamined published application)) but they are not suitable for use in applications where high mechanical strength is required.

There are many metallic members that require high physical and chemical strength, large surface areas and a high capacity for anchoring the coating material they include, in addition to the electrode substrate described above, carrier supports for use in chemical reactors and metallic materials for biocompatible implants such as artificial bones. However, no titanium-based materials have been developed to date that satisfy all of the requirements for use in these applications.

SUMMARY OF THE INVENTION

One object, therefore, of the present invention is to provide a titanium or titanium alloy composite having improved physical and chemical strength, which has a large surface area and exhibits a great capacity to anchor a coating material.

Another object of the present invention is to pro vide a process that is capable of readily producing a titanium or titanium alloy composite having such superior characteristics.

In order to attain these objects, the present invention provides a process for producing a titanium or titaniun alloy composite having a porous surface layer, comprising: providing a coating composition comprising a binder added to a mixture of a titanium or titanium alloy powder and a magnesium power; then applying said composition to the surface of a titanium or titanium alloy substrate; heating the substrate either in vacuo or an inert atmosphere so as to form a sintered product of titanium or titanium alloy and magnesium powders which firmly adheres to the substrate, and subsequently removing magnesium from the sintered product.

BRIEF DESCRIPTION OF THE DRAWING

The FIGURE is a micrograph showing a cross section of a titanium composite sample prepared in accordance with the present invention.

DETAILED DESCRIPTION OF THE INVENTION

In the present invention, elemental titanium is typically used as a substrate material but, if a specific use requires, titanium alloys containing other metals such as Ta, Nb, platinum group metals, Al and V may be employed. The substrate shaped into a plate, rod or any other appropriate form is preferably subjected to a surface-cleaning treatment by-washing with wazer, acids, ultrasonic waves or steam. If desired, the clean surface of the substrate may be roughened by combinations of suitable known techniques such as etching and blasting.

The titanium substrate with a clean surface is subsequently treated to have a porous titanium or titanium alloy layer adhered to its surface by the following procedures: first, a powder of titanium or alloy thereof containing one or more of the elements mentioned above is mixed with an appropriate amount of magnesium powder; a suitable amount of binder is added to the mixture to prepare a coating composition; the coating composition is applied to the titanium substrate, followed by drying if desired, and heated either in vacuo or in an inert atmosphere such as argon so that an adhering sintered body of titanium or titanium alloy and magnesium is formed on the substrate surface. Heating of the substrate is preferably carried out at a temperature not lower than the melting point of magnesium (650° C). At this temperature magnesium is melted and a sintering reaction takes place with titanium or an alloy thereof in a liquid phase. The heating temperature is preferably not higher than about 800° C. because beyond this temperature magnesium evaporates in an undesirably large amount. The temperature range of from 650 to 800° C. may be maintained for a suitable period which is typically between 1 and 3 hours.

The titanium powder from which a sintered body is to be obtained is usually made of metallic titanium but it may be a powder of hydrogenated titanium. Powders of such titanium compounds that readily undergo thermal decomposition into metallic titanium are included within the category of the "titanium powder" which is to be sintered with a magnesium powder. Powders of titanium alloys may be used as long as the alloying components will not selectively melt in magnesium, and an example of a suitable titanium alloy is Ti-Al-V. The particle size of the titanium powder is not limited to any particular value and may be selected from the range of several microns to several millimeters according to the specific use of the product.

In order to form a porous titanium layer having a desired porosity and pore size, the titanium powder is mixed with a magnesium powder that has an appropriately selected particle size and which is used in a suitably selected mixing ratio. Typically, a magnesium powder having a particle size of from 100 to 2,000 μm is used in a volume ratio of from 5 to 75% of the powder mixture.

The mixed powder is blended with a binder such as CMC (carboxymethyl cellulose), collodion or polyvinyl alcohol, or water or an organic solvent, and the resulting coating composition in a paste form may be applied to the substrate by spray coating or brushing or with a variety of coaters well known to those skilled in the art so as to form a coating of a desired thickness. The amount of the binder used in the coating composition can be readily determined by those skilled in the art.

The sintered layer adhering onto the titanium substrate is then freed of magnesium so as to provide the desired titanium composite having a porous surface. Removal of the magnesium content may be achieved by a variety of physical or chemical means which can be readily determined by those skilled in the art. In one method, use is made of the difference between the melting points of titanium and magnesium by heating the sintered body either in vacuo or in an inert atmosphere such as argon at a temperature not lower than one employed in the formation of the sintered body. Satisfactory results are typically attained by heating the sintered body at temperatures of 1,000° C. or below. Another advantageous method is selective dissolving away of magnesium that is achieved either by contacting the sintered body with an acidic solution that dissolves metallic magnesium but hardly dissolves titanium or alloys thereof or by immersing said sintered body in said acidic solution. Examples of suitable acidic solutions include organic acids and inorganic acids such as sulfuric acid, hydrochloric acid, nitric acid and phosphoric acid.

By following the procedures outlined above, a porous titanium body having a three-dimensional skeletal structure is obtained as a layer that strongly adheres onto the titanium substrate through metal fusion at the interface and the resulting titanium composite with a porous surface has a large surface area and displays satisfactory anchor effects. The FIGURE is a micrograph (magnification: about 8.3x) showing a cross section of a titanium composite sample produced by the method of the present invention.

The advantages of the present invention are hereunder described by illustrative working examples to which the scope of the invention is by no means limited.

Unless otherwise specified, all percents, ratios, etc. are by weight.

EXAMPLE 1

A rolled strip of Ti-6A1-4V alloy measuring 25 mm x 15 mm x 3 mm was cleaned with ultrasonic waves in acetone and etched in boiling 20% HCl to prepare a substrate. In a separate step, a titanium powder having a particle size of 44 μm or below and a magnesium powder of from 250 to 710 μm in size were mixed in a volume ratio of 1/1. A small amount of a 1.5% aqueous solution of CMC was added to the powder mixture to prepare a coating composition in a paste form.

The coating composition was applied to the titaniun alloy substrate to a thickness of about 3 mm. After air drying, the substrate was heated at 700° C. in an argon atmosphere for 2 hours to form a sintered body of titanium and magnesium that adhered strongly onto the substrate. The sintered body was heated to 950° C. at which temperature it was held for 2 hours so that substantially all of the magnesium present evaporated from the sintered body to yield a titanium composite having a porous surface.

Both the surface and cross section of the obtained titanium composite were observed with a stereomicroscope. As shown in the FIGURE, the porous titanium layer 2 adhering to the substrate 1 contained many pores that were closer in size to the particle size of the magnesium powder used and which communicated with one another to form a satisfactorily strong three-dimensional skeletal structure similar to that of spongy titanium. This layer 2 formed a continuous phase at the interface with the substrate 1 and exhibited an extremely strong adhesion to the substrate.

EXAMPLE 2

A pure titanium plate measuring 25 mm x 15 mm x 1 mm was blasted with alumina sand (average grain size =0.7 mm) to provide a roughened surface. The Ti plate was then pickled in boiling 20% HCl. In a separate step, titanium sponge was ground into particles of 5 μm or smaller in size in amyl alcohol. To the resulting Ti powder, an amyl alcohol suspension of a magnesium powder (10 to 50 μm in size) and a small amount of colloidion binder were added and the mixture was thoroughly stirred to form a slurry of coating composition containing amyl alcohol as a solvent.

The slurry was applied to the titanium substrate to a thickness of about 1 mm and subsequently dried in an argon atmosphere. The dried substrate was sintered by heating in water-free argon gas at 660 to 680° C. for 2 hours. After cooling, the substrate was immersed in a 15% $H_2SO_4$ aqueous solution for 2 hours so that magnesium was dissolved away from the sintered body, yielding a titanium composite having a porous Ti surface layer in a thickness of about 0.5 mm.

Electrodes for electrolysis were fabricated by pyrolytic coating of ruthenium oxide on substrates made of the Ti composite prepared in accordance with the present invention. The anode potential measured in saturated aqueous sodium chloride at a current density of 30 $A/dm^2$ was 35 mV lower than the value occurring for an electrode that was fabricated by coating a ruthenium oxide film on a titanium substrate which did not have any porous surface layer. This showed that the titanium composite having a porous surface in accordance with the present invention would provide an electrode substrate having an effective surface area about 10 times as large as that of the conventional smooth-surfaced titanium plate. In addition, the porous surface layer formed in accordance with the present invention had satisfactorily high levels of mechanical strength and adhesion to the substrate so that it could be handled in practical applications as roughly as titanium plates.

The present invention provides a titanium composite having a porous surface that exhibits improved physical and chemical strength and which has a large surface area and displays a great capability of anchoring a coating material This composite is highly useful as an electrode substrate, a catalyst support or as a metallic material for biocompatible implants. In accordance with the present invention, a mixed powder of titanium and magnesium is sintered in a liquid phase, and the sintered product may be either heated at low temperatures not exceeding 1,000° C. or treated with an acidic solution so as to remove any residual magnesium from the sinter. This provides a simple way to attain a titanium substrate to which a porous titanium layer having a desired thickness and porosity adheres strongly.

While the invention has been described in detail and with reference to specific embodiments thereof, it will be apparent to one skilled in the art that various changes and modifications can be made therein without departing from the spirit and scope thereof.

What is claimed is:

1. A process for producing a titanium or titanium alloy composite having a porous surface layer, comprising:

providing a coating composition comprising a binder added to a mixture of a titanium or titanium alloy powder and a magnesium powder, wherein said magnesium powder is present in an amount of from 5 to 75% by volume of the powder mixture and has a particle size of from 100 to 2,000 μm;

applying said composition to the surface of a titanium or titanium alloy substrate;

heating the substrate at a temperature of from 650 to 800° C. in vacuo or an inert atmosphere so as to form a sinter of the powders of titanium or titanium alloy and magnesium which firmly adheres to said substrate; and removing magnesium from said sinter.

2. A process as in claim 1, wherein the removal of magnesium from the sinter is achieved by evaporation through heating at a temperature not lower than the sintering temperature and not higher than 1,000° C.

3. A process as in claim 1, wherein the removal of magnesium from the sinter is achieved by allowing the magnesium to dissolve away in an acidic solution.

* * * * *